United States Patent [19]

Neigel

[11] Patent Number: 4,642,389

[45] Date of Patent: Feb. 10, 1987

[54] PROCESS FOR THE MANUFACTURE OF CHLOROACETALDEHYDE DIALKYL ACETALS

[75] Inventor: Dennis Neigel, Whitehouse Station, N.J.

[73] Assignee: National Starch and Chemical Corporation, Bridgewater, N.J.

[21] Appl. No.: 868,456

[22] Filed: May 30, 1986

[51] Int. Cl.$^4$ .................. C07C 41/48; C07C 41/58; C07C 41/50

[52] U.S. Cl. .................................................. 568/604

[58] Field of Search ........................................ 568/604

[56] References Cited

U.S. PATENT DOCUMENTS

| | | | |
|---|---|---|---|
| 2,330,570 | 9/1943 | Filachione | 260/615 |
| 2,411,826 | 11/1946 | Filachione | 260/615 |
| 2,803,668 | 8/1957 | Morris et al. | 260/615 |
| 4,130,592 | 12/1978 | Vogt et al. | 568/604 |
| 4,440,959 | 4/1984 | Deinhammer | 568/604 |

OTHER PUBLICATIONS

Filachione, E. M., Am. Chem. Soc., vol. 61, 1939, pp. 1705–1706.

Primary Examiner—Howard T. Mars
Attorney, Agent, or Firm—Edwin M. Szala; Ellen T. Dec

[57] ABSTRACT

A semi-continuous process for the manufacture of acetals of alpha-halogenated aldehydes is described. In a preferred embodiment of the invention, chloroacetaldehyde dimethyl acetal is prepared by introducing chlorine and a mixture of vinyl acetate and an excess of methanol through separate inlets into a reaction site of a vertical packed column and collecting a low boiling distillate formed from by-product vapors and separately collecting the crude acetal product flowing downward from the reaction site.

16 Claims, 1 Drawing Figure

PROCESS FOR THE MANUFACTURE OF CHLOROACETALDEHYDE DIALKYL ACETALS

BACKGROUND OF THE INVENTION

This invention relates to a new process for the manufacture of acetals of alpha-halogenated aldehydes. More particularly, it relates to an improved process for the manufacture of chloroacetaldehyde dimethyl acetal.

A number of processes for the manufacture of chloroacetaldehyde acetals are known and have been disclosed in the prior art. For example, Ullman, Enzyklopadie der technischen Chemie, 4th edition 1975, vol. 9 page 375, describes the manufacture of chloroacetaldehyde acetals by chlorinating vinyl compounds in alcoholic medium. U.S. Pat. No. 2,803,668 and also U.S. Pat. No. 4,130,592 teach the chlorination of vinyl chloride which produces considerable amounts of 1,1,2-trichlorethane as a by-product. Because of its similar boiling point, it is difficult to separate the by-product from the desired chloroacetaldehyde dimethyl acetal. Moreover, a particular disadvantage of these methods relate to the highly toxic nature of the vinyl chloride starting material.

The reaction of vinyl acetate and a halogen in the presence of excess alcohol has been known for many years: see U.S. Pat. Nos. 2,330,570 and 2,411,826 and Am. Chem. Soc., vol. 61 (1939) pages 1705–1706 by E. M. Filachione. The acetals were isolated from the reaction mixture by customary methods, e.g. by the addition of water and by subsequent extraction of the acetal layer with a water-immmiscible solvent such as ether, chloroform or benzene. The organic extract was washed with water and/or an aqueous alkaline solution, such as sodium bicarbonate solution, in order to remove acid or other water-soluble by-products, after which the organic solvent was then distilled off and the acetal purified by distillation. Because of relatively poor yields (approximately 46 to 53%) and also that large amounts of solvent have to be distilled, the process is inappropriate for the manufacture of chloroacetaldehyde dimethyl acetal on an industrial scale.

U.S. Pat. No. 4,440,959 issued Apr. 3, 1984 to Wacker-Chemie Gmbh relates to an improved process for the manufacture of chloroacetaldehyde dimethyl acetal by reacting vinyl acetate and chlorine in a methanolic solution at a temperature of less than 20° C. When the addition of chlorine is completed, low boiling constituents are partially or completely distilled off from the reaction mixture. The liquid residue is neutralized with solid oxides or carbonates of calcium and magnesium while maintaining a temperature of from 20° to 60° C. until the aqueous extract has a pH of greater than 5. When neutralization is completed, the reaction mixture forms two liquid phases and the upper organic layer containing the desired product is separated and fractionally distilled. The patent states that pure chloroacetaldehyde dimethyl acetal is obtained as the main fraction with yields of more than 90% calculated on the amount of vinyl acetate.

The process described in U.S. Pat. No. 4,440,959 is a batch-type operation and none of the prior art applicant is aware of, relating to the production of such compounds, teaches or suggests the use of a continuous or semi-continuous process.

Particularly where large scale industrial operations are contemplated, there is a need for a safe and economical, continuous process for the manufacture of acetals of alpha halogenated aldehydes.

The acetals described herein are useful as intermediates in the production of other compounds which have commercial uses.

SUMMARY OF THE INVENTION

In accordance with the process of the present invention, acetals of alpha-halogenated aldehydes can be manufactured by a semi-continuous process in which elemental chlorine or bromine is contacted in a reaction site of a vertical packed column with a mixture of vinyl acetate and an excess of methanol. In the use of the term "semi-continuous" herein, it is intended to mean a continuous process with respect to the formation of the crude acetal product and a batch-type process with respect to the isolation of the acetal from the reaction product mixture and its subsequent purification.

It is noted that the semi-continuous process herein is equally feasible with either chlorine or bromine although the higher price of the latter halogen encourages use of chlorine. For convenience in the remainder of the specification and claims, where reference is made to chlorine, it is intended to mean either chlorine or bromine.

The reaction of chlorine with the mixture of vinyl acetate and methanol is substantially instantaneous and is run as a continuous reaction process. The chlorine and vinyl acetate/methanol mixture are fed through separate inlets (ports) in stoichiometric amounts with respect to the chlorine and vinyl acetate and enter into an exothermic reaction which provides and maintains temperatures greater than about 55° C., preferably 56°–58° C., at the reaction site. Low boiling by-products are vaporized by the exothermic heat of reaction and collected as a distillate. The higher boiling acetal product formed within the column remains as a liquid which flows down the column and is collected in a suitable cooled receiver. When the crude acetal is collected in the bottoms receiver in an amount convenient for further working, the feed of starting materials is cut and the reaction is terminated. To avoid the need for terminating the reaction, the bottoms receiver can be fitted with a discharge valve so that the receiver could be discharged on a continuous or semi-continuous basis. As will be made clear in the description of the invention that follows, the work-up of the crude acetal to yield the purified product is accomplished by known, batch-type procedures.

By utilizing this semi-continuous process, a number of benefits are realized over batch-type processes of the prior art. Thus, improved economics and efficiencies are obtained because the heat of reaction is used herein to vaporize and isolate the by-products, thereby reducing the need for external energy input. Improved safety is obtained since relatively small amounts of reactant chemicals are under process at the reaction site at any given time as compared to batch-type operations. Improved process control is obtained since the continuous system has a number of operating parameters, for example, feed rate and column height, which can be adjusted to maximize conversion and operating efficiency.

DESCRIPTION OF THE PREFERRED EMBODIMENTS

Figure 1:
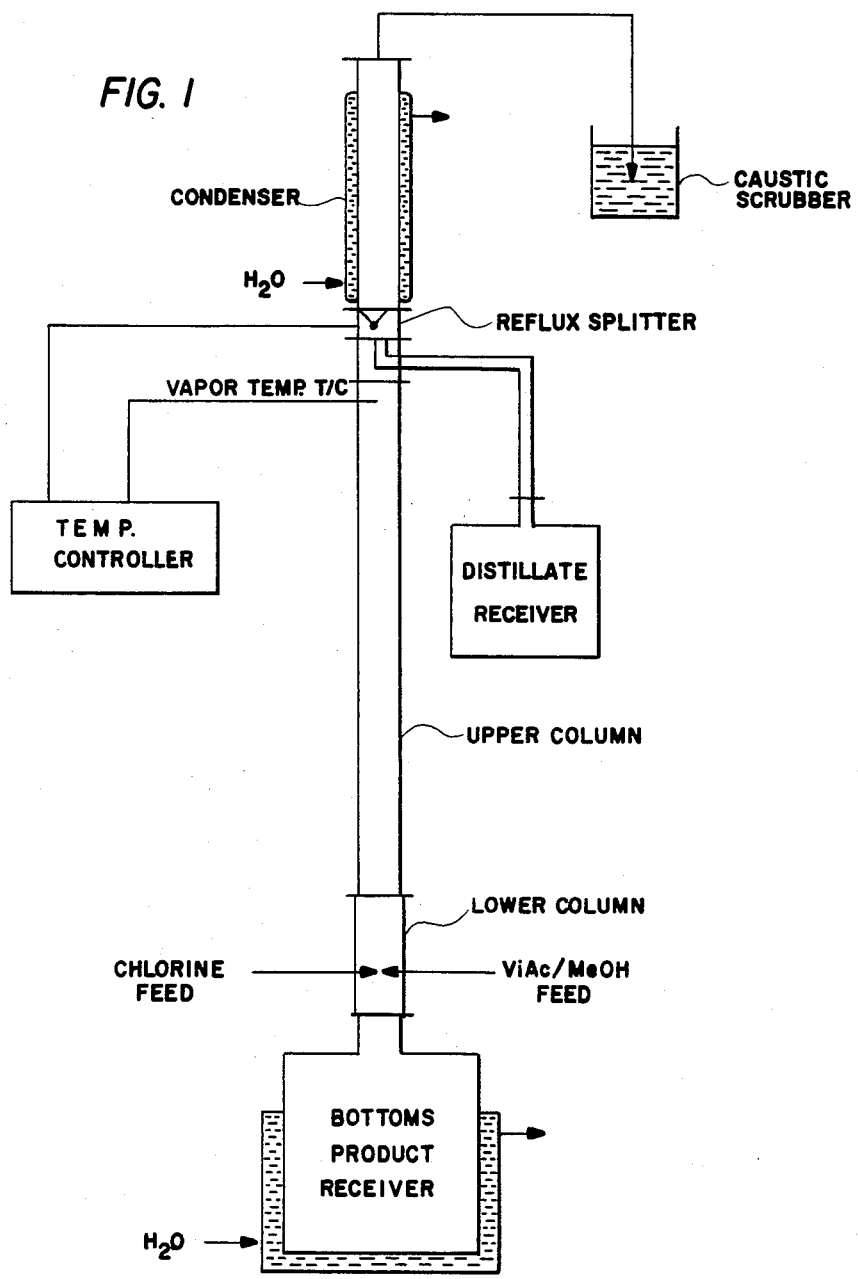

With respect to apparatus, accompanying FIG. 1 schematically shows two suitably fitted columns arranged to carry out the process of the present invention.

Thus, the process of this invention requires a vertical, packed column reactor with two side entry ports to permit the continuous addition of the chlorine gas in one port and the addition in the other port of the liquid mixture of vinyl acetate and methanol. In FIG. 1 this reactor is termed the "lower column". The lower opening of this column is fitted with a cooled bottoms product receiver which is adapted to collect the crude acetal product. The upper opening of the column is fitted with another packed column (ordinarily, about 1× to 2× the length of the lower column). The upper opening of the "upper column" is suitably fitted with a reflux splitter, vapor temperature thermocouple, water cooled condenser and distillate receiver. The condenser is adapted to permit residual vapors to escape into a caustic scrubber.

The packing used in the lower and upper column preferably is of the ceramic saddle type, although glass beads, plastic honeycomb and other common, corrosion resistant packing materials can also be used. The two columns, reflux splitter and condenser will ordinarily be glass lined or be made of glass or other material able to withstand the corrosive properties of the chemicals used and formed in the present process. The two columns may optionally be vacuum jacketed to prevent loss of heat. While FIG. 1 schematically shows apparatus useful in carrying out the process herein, the invention is not limited to the illustrated apparatus described above. For example, one vertical, packed column having two side entry ports at the lower portion, and suitably fitted at the lower opening with a cooled bottoms product receiver and the upper opening fitted with a reflux splitter, vapor temperature thermocouple, a water cooled condenser and distillate receiver may be used in place of a "lower" and "upper" column. Significant variations or modifications in the apparatus will not necessarily change or destroy the described semi-continuous process of the invention.

In the manufacture of chloroacetaldehyde dimethyl acetal in accordance with the process of this invention, a flow of chlorine gas is brought in contact with a liquid feed of a mixture of vinyl acetate and methanol. The two feed components are introduced through separate inlets into a reaction site of a vertical packed lower column where the components enter into an exothermic reaction. For proper reaction to occur, it is necessary that the vinyl acetate be mixed with an excess of methanol to provide the vinyl acetate/methanol mixture. Ordinarily, the mixture will consist of from 3.5 to 6 moles of methanol to 1 mole of vinyl acetate, preferably about 4 to 4.5 moles of methanol to 1 mole of vinyl acetate. Use of absolute methanol, i.e., dry methanol, is preferred. The chlorine and vinyl acetate/methanol are fed in stoichiometric amounts at constant rates measured in moles/minute so that one mole of chlorine is available to react with one mole of vinyl acetate.

The rate of feeding the column reaction site is mainly governed by the size of the apparatus in which the process is run. For example, the inner diameter of the packed columns as well as their height will be strong factors in determining the parameter of feeding the starting chemicals to the reaction site. As a useful guideline, when the process is run in columns having an inner diameter of 50 mm with a (combined) height of about 110–120 cm, the chlorine and vinyl acetate reactants can be fed at a rate of about 0.06 to 0.08 moles/minute. Practitioners will be able to adjust the feed to suitable rates with no difficulty.

When the process is started by the flow of reactants to the reaction site, the heat of reaction will provide sufficient heat to vaporize the low boiling by-products, mainly methyl acetate, methanol and aqueous hydrochloric acid. The low boiling vapors will pass upward within the upper packed column where reflux splitter means are provided to collect the distillate having a boiling point of less than about 70° C. and preferably less than about 56°–57° C. Collecting distillate with the reflux splitter set at the higher temperature within the above range will provide a higher concentration of crude acetal in the bottoms receiver. Conveniently, the distillate can be collected with the help of a reflux splitter which is connected with external means of controlling the reflux split at a desired temperature. Ordinarily, the upper opening of the column carrying the reflux splitter is fitted with a water cooled condenser where residual vapors are directed through to an aqueous caustic scrubber. In order to maintain economical production of the acetal, the distillate may be worked to recover methanol which may be recycled into the process. In doing so, the distillate is adjusted to a pH of 10.0–10.2 with aqueous sodium hydroxide and thereafter fractionally distilled to provide a good recovery of methanol.

The heat of reaction will also provide sufficient heat for the crude acetal product to partly reflux in the packed column where a liquid-vapor equilibrium develops in which the liquid crude acetal (so-called "bottoms") flows downward from the reaction site into a cooled receiver attached to the lower packed column.

The acetal may be recovered from the crude acetal reaction mixture by any of several convenient, known procedures. Thus, in one such procedure, calcium oxide or calcium hydroxide is added to the mixture to provide a pH greater than 3, preferably 3.1–3.4, and to produce two phases: an upper organic layer and a lower aqueous layer. The upper layer containing the product can now be purified either by fractional distillation or by the addition of 20–30% aqueous sodium hydroxide and subsequent phase separation of chloroacetaldehyde dimethyl acetal from the hydrolyzed methyl acetate to yield high purity product.

The following examples illustrate the process of this invention although it will be understood that these examples are included for purposes of illustration and are not intended to limit the scope of the invention.

EXAMPLE 1

Apparatus similar to that illustrated in FIG. 1 was assembled to provide the means of running the semi-continuous process for the manufacture of chloroacetaldehyde dimethyl acetal.

A vacuum jacketed, glass, upper column (50 mm inner diameter, 80 cm height) was packed with ceramic saddles and fitted, at the upper opening, with a reflux splitter, vapor temperature thermocouple and overhead condenser/receiver. The receiver contained an aqueous caustic solution. At the lower opening of the upper column, a lower column (50 mm inner diameter, 30 cm height) was connected, which column was similarly jacketed and packed and contained 2 side entry ports permitting continuous chemical addition. One port was fitted for the measured addition of chlorine while the other port was fitted to permit the measured addition of the vinyl acetate/methanol mixture.

In starting the process, a feed comprising a mixture of vinyl acetate, 860 g. (10 moles) and absolute methanol 1280 g. (40 moles) was added through one entry port at a constant rate of 14.3 g./min. Simultaneously, the addition of chlorine gas through the other port was started at a constant rate of 4.7 g./min. The reflux splitter was set to remove condensate from the system only when the vapor temperature at the top of the upper column read <57° C. The process was run continuously for about 2.5 hours operating at the described conditions, and was thereafter terminated by closing the flow of chlorine and the vinyl acetate/methanol mixture.

The collected distillate comprising an acidic mixture of methyl acetate and methanol (684 g.) was neutralized with aqueous sodium hydroxide to a pH of 10.0-10.2 and then fractionally distilled to reclaim 384 g. (12 moles) of methanol.

The crude acetal reaction product collected in the bottoms product receiver (1,800 g.) was neutralized with 286 g. of calcium oxide to a pH of 3.1-3.3. The neutralized mixture was phase separated (employing a separatory funnel) to form an upper product layer of 1452 g. of 70.3% chloroacetaldehyde dimethyl acetal (82% yield). The upper product layer was thereafter fractionally distilled under reduced pressure to yield 1,000 g. of chloroacetaldehyde dimethyl acetal, b.p. 55° C. at 50 mm Hg, of greater than 99% purity measured by gas chromatography. The pure compound has a refractive index of 1.4148±0.0005 at 20° C. and a specific gravity of 1.09-1.10 at 25° C.

EXAMPLE 2

The process of Example 1 was repeated except that the reflux splitter was set to remove condensate when the vapor temperature at the top of the upper column read <60° C. The concentration of chloroacetaldehyde dimethyl acetal in the resultant product layer was raised to 75%.

EXAMPLE 3

The process of Example 1 was repeated except that calcium hydroxide (377 g.) was used in place of calcium oxide in neutralizing the crude acetal product.

EXAMPLE 4

The process of Example 1 was repeated except that the neutralized product layer was treated with 800 g. (5 moles) of 25% aqueous sodium hydroxide to a pH of 10.0-10.2 at 50° C. ±5° C. in place of fractional distillation. This mixture was allowed to phase separate to provide an upper layer of greater than 95% chloroacetaldehyde dimethyl acetal without distillation.

While the process has been described in terms of being carried out in an open system at atmospheric pressures, it is contemplated that the process can also be carried out in a closed system at reduced pressures and temperatures with only minor modifications. Thus, where certain temperatures are required in the process run at ambient pressures, the practitioner can reduce the pressure in the system as desired, for example, preferably to 100-300 mm Hg., and readily calculate the corresponding temperatures for running the process. Use of a closed system will ordinarily improve the yield of product.

In operating the process at reduced pressures, the methanol used herein can be replaced with other alcohols, for example, ethanol, isopropanol, n-propanol, and the like, with only minor modifications which will be apparent to the practitioner. Use of such alcohols would provide the corresponding dialkyl acetal.

Now that the preferred embodiments of the present invention have been described in detail, various modifications and improvements thereon will become readily apparent to those skilled in the art. Accordingly, the spirit and scope of the invention are to be limited only by the appended claims and not by the foregoing specification.

What is claimed is:

1. A semi-continuous process for the manufacture of chloroacetaldehyde dimethyl acetal comprising the steps of:
   (a) providing a vertical packed column, having side by side inlets, means for collecting a low-boiling distillate and a water-cooled condenser connected at the upper end and a cooled bottoms receiver connected at the lower end,
   (b) introducing chlorine and a mixture of vinyl acetate and an excess of methanol at a constant rate and stoichiometric amounts with respect to chlorine and vinyl acetate through the separate inlets into a reaction site of the vertical packed column, wherein an exothermic reaction provides and maintains a temperature at the site of about 56°-58° C.,
   (c) collecting a low boiling distillate formed from the vapors having a boiling point less than about 70° C., and
   (d) collecting the crude acetal liquid product flowing downward from the reaction site in a cooled bottoms receiver.

2. The process of claim 1 wherein the mixture of vinyl acetate and methanol contains from 3.5-6 moles of methanol per mole of vinyl acetate.

3. The process of claim 1 wherein the means for collecting a low-boiling distillate comprises a reflux-splitter and thermocouple control.

4. The process of claim 3 wherein the thermocouple control is set to collect distillate having a boiling point less than about 57° C.

5. The process of claim 1 wherein the crude acetal product collected in the bottoms receiver is treated with calcium oxide or calcium hydroxide to a pH of 3.1 to 3.4, the product layer is separated from the aqueous layer and fractionally distilled under reduced pressure to yield purified chloroacetaldehyde dimethyl acetal.

6. The process of claim 1 wherein the vertical packed column is a glass column and contains glass beads or ceramic, saddle-type packing.

7. The process of claim 6 wherein the vertical packed column is a combination of one vertical packed column connected to another vertical packed column.

8. In a semi-continuous process for the manufacture of chloroacetaldehyde dimethyl acetal including the steps of reacting chlorine with a mixture of vinyl acetate and a molar excess of methanol and subsequently isolating the chloroacetaldehyde dimethyl acetal from the crude reaction product, the improvement comprising the steps of:
   (a) feeding continuously chlorine and a mixture of vinyl acetate and methanol through separate inlets into a reaction site of a lower vertical packed column, wherein the chlorine and vinyl acetate are fed in stoichiometric amounts at a rate where the exothermic reaction provides and maintains a reaction temperature greater than about 55° C.,
   (b) directing vapors of low boiling by-products upward through an upper packed column and reflux splitter and water-cooled condenser connected thereto, and collecting as distillate by-products having a boiling point less than about 70° C. and (c) collecting the flow of crude acetal product from the reaction site in a cooled bottoms receiver attached to the lower packed column.

9. The process of claim 8 where the mixture of vinyl acetate and methanol contains from 3.5 to 6 moles of methanol per mole of vinyl acetate.

10. A semi-continuous process for the manufacture of chloroacetaldehyde dialkyl acetal comprising the steps of:

(a) providing a closed system for operating at reduced pressures comprising a vertical packed column having side by side inlets, means for collecting a low-boiling distillate and a water-cooled condenser connected at the upper end and a cooled bottoms receiver connected at the lower end, (b) introducing into the reduced pressure system chlorine and a mixture of vinyl acetate and an excess of alcohol at a constant rate and stoichiometric amounts with respect to chlorine and vinyl acetate through the separate inlets into a reaction site of the vertical packed column, wherein the alcohol is selected from the group of methanol, ethanol, propanol and isopropanol;

(c) collecting a low-boiling distillate formed from the by-product vapors; and (d) collecting the crude acetal liquid product flowing downward from the reaction site in a cooled bottoms receiver.

11. The process of claim 10 wherein the alcohol is methanol and the mixture of vinyl acetate and methanol contains from 3.5 to 6 moles of methanol per mole of vinyl acetate.

12. The process of claim 11 wherein the pressure in the closed system is between 100–300 mm Hg. and the temperature at the reaction site corresponds to 56°–58° C. at ambient pressure.

13. The process of claim 12 wherein the means for collecting a low-boiling distillate comprises a reflux splitter and thermocouple control.

14. The process of claim 13 wherein the thermocouple control is set to collect distillate having a boiling point corresponding to less than about 70° C. at ambient pressure.

15. The process of claim 10 wherein the crude acetal product collected in the bottoms receiver is treated with calcium oxide or calcium hydroxide to provide a pH of 3.1 to 3.4, the product layer is separated from the aqueous layer and fractionally distilled under reduced pressure to yield purified chloroacetaldehyde dialkyl acetal.

16. The process of claim 10 wherein the crude acetal product collected in the bottoms receiver is treated with calcium oxide or calcium hydroxide to provide a pH of 3.1–3.4, the product layer is separated from the aqueous layer and treated with aqueous sodium hydroxide, and the upper layer is separated from the aqueous layer to yield high purity, chloroacetaldehyde dialkyl acetal.

* * * * *